US00PP32681P3

(12) United States Plant Patent
Post

(10) Patent No.: US PP32,681 P3
(45) Date of Patent: Dec. 22, 2020

(54) ***CHRYSANTHEMUM* PLANT NAMED 'DLFGAVI7'**

(50) Latin Name: ***Chrysanthemum* X *morifolium***
Varietal Denomination: DLFGAVI7

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,328

(22) Filed: Mar. 19, 2020

(65) Prior Publication Data

US 2020/0305324 P1 Sep. 24, 2020

Related U.S. Application Data

(60) Provisional application No. 62/919,611, filed on Mar. 20, 2019.

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./287, 293
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'DLFGAVI7', characterized by its upright plant habit; vigorous growth habit; dark green-colored leaves; uniform flowering habit; strong upright flowering stems typically grown as a single-stem (disbudded) cut flower; decorative-type inflorescences with dark red purple-colored ray florets; and relative resistance to *Fusarium oxysporum* f. sp. *chrysanthemi, Verticillium dahliae* and *Puccinia horiana* strain PhNL1.

2 Drawing Sheets

Figure 1:
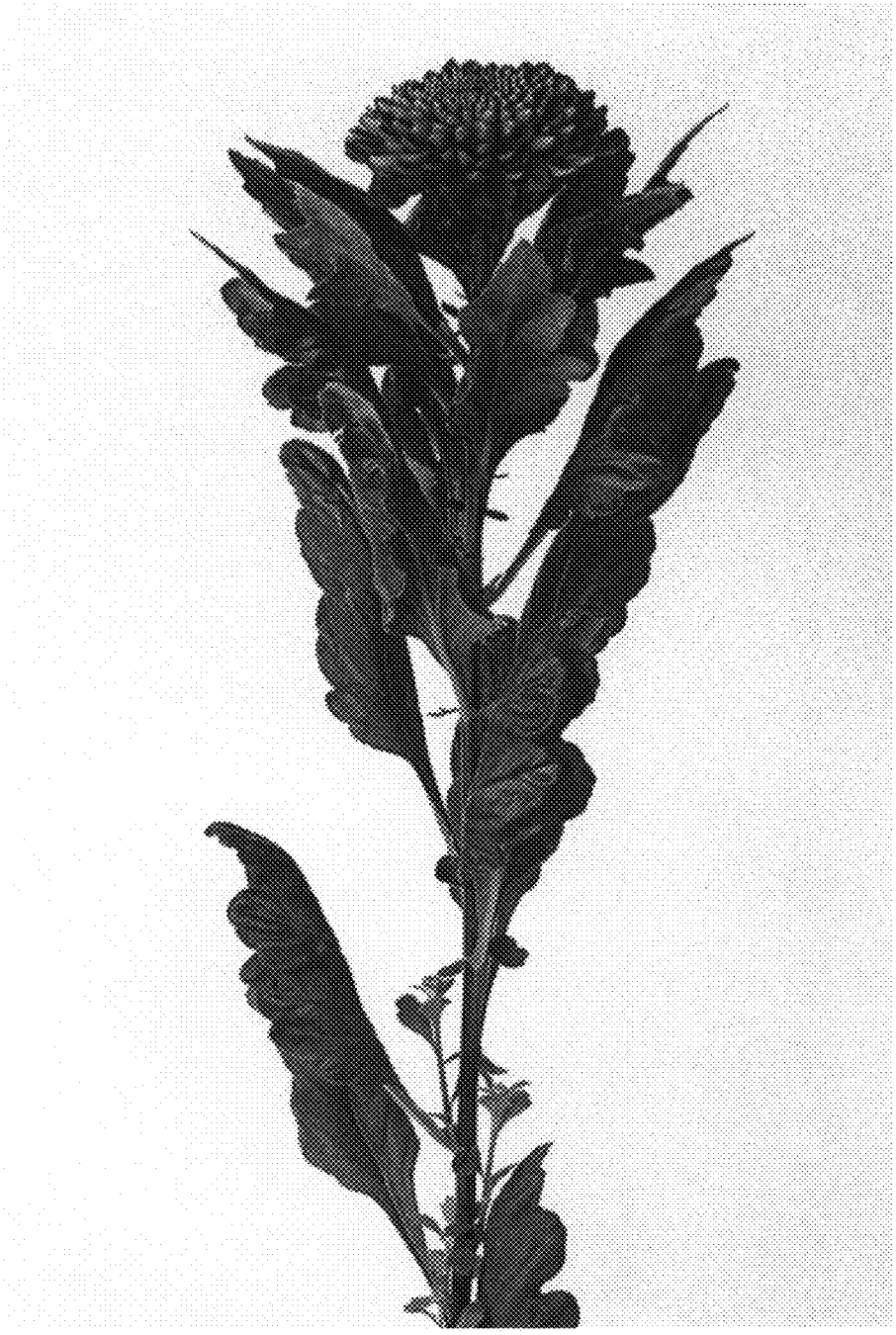

Botanical designation: *Chrysanthemum* X *morifolium*.
Cultivar denomination: 'DLFGAVI7'.

CROSS-REFERENCED TO CLOSELY-RELATED APPLICATIONS

Title: Varieties of *Chrysanthemum* Plants
Inventor/Applicant: Arie Gerard Post
Filed: Mar. 20, 2019
Ser. No.: 62/919,611
Inventor/Applicant hereby claim the benefit of this provisional U.S. Patent Application.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFGAVI7'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in February, 2015 of a proprietary selection of *Chrysanthemum* x *morifolium* identified as code number DB 33586 as the female, or seed, parent with a proprietary selection of *Chrysanthemum* x *morifolium* identified as code number DB 11247 as the male, or pollen, parent. The new *Chrysanthemum* plant was discovered and selected as a single flowering plant from within the progeny of the stated cross-pollination in a controlled greenhouse environment in Maasdijk, The Netherlands in March, 2016.

Asexual reproduction of the new *Chrysanthemum* plant by vegetative terminal cuttings since March, 2016 in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFGAVI7'. These characteristics in combination distinguish 'DLFGAVI7' as a new and distinct *Chrysanthemum* plant:

1. Upright plant habit; vigorous growth habit.
2. Dark green-colored leaves.
3. Uniform flowering habit.
4. Strong upright flowering stems typically grown as a single-stem (disbudded) cut flower.
5. Decorative-type inflorescences with dark red purple-colored ray florets.
6. Relatively resistant to *Fusarium oxysporum* f. sp. *chrysanthemi, Verticillium dahliae* and *Puccinia horiana* strain PhNL1.

Plants of the new *Chrysanthemum* differ from plants of the female parent selection in inflorescence size as plants of the new *Chrysanthemum* have smaller inflorescences than plants of the female parent selection. In addition, plants of the new *Chrysanthemum* have dark red-colored ray florets whereas plants of the female parent selection have dark purple-colored ray florets.

Plants of the new *Chrysanthemum* differ from plants of the male parent selection in ray floret color as plants of the new *Chrysanthemum* have dark red-colored ray florets whereas plants of the male parent selection have purplish red-colored ray florets. In addition, ray florets of plants of the new *Chrysanthemum* are slightly revolute whereas ray florets of plants of the male parent selection are strongly revolute.

Plants of the new *Chrysanthemum* can be compared to plants of *Chrysanthemum* X *morifolium* 'Delibarca', not patented. In side-by-side comparisons plants of the new *Chrysanthemum* differ primarily from plants of 'Delibarca' in ray floret color as ray florets of plants of the new *Chrysanthemum* have dark red in color whereas ray florets of plants of 'Delibarca' are dark purplish red in color. In addition, apices of ray florets of plants of the new *Chrysanthemum* are obtuse to retuse whereas apices of ray florets of plants of 'Delibarca' are mammillate.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1 of 2) comprises a side perspective view of a typical flowering stem of 'DLFGAVI7' grown as a disbud-type cut flower.

Figure 2:
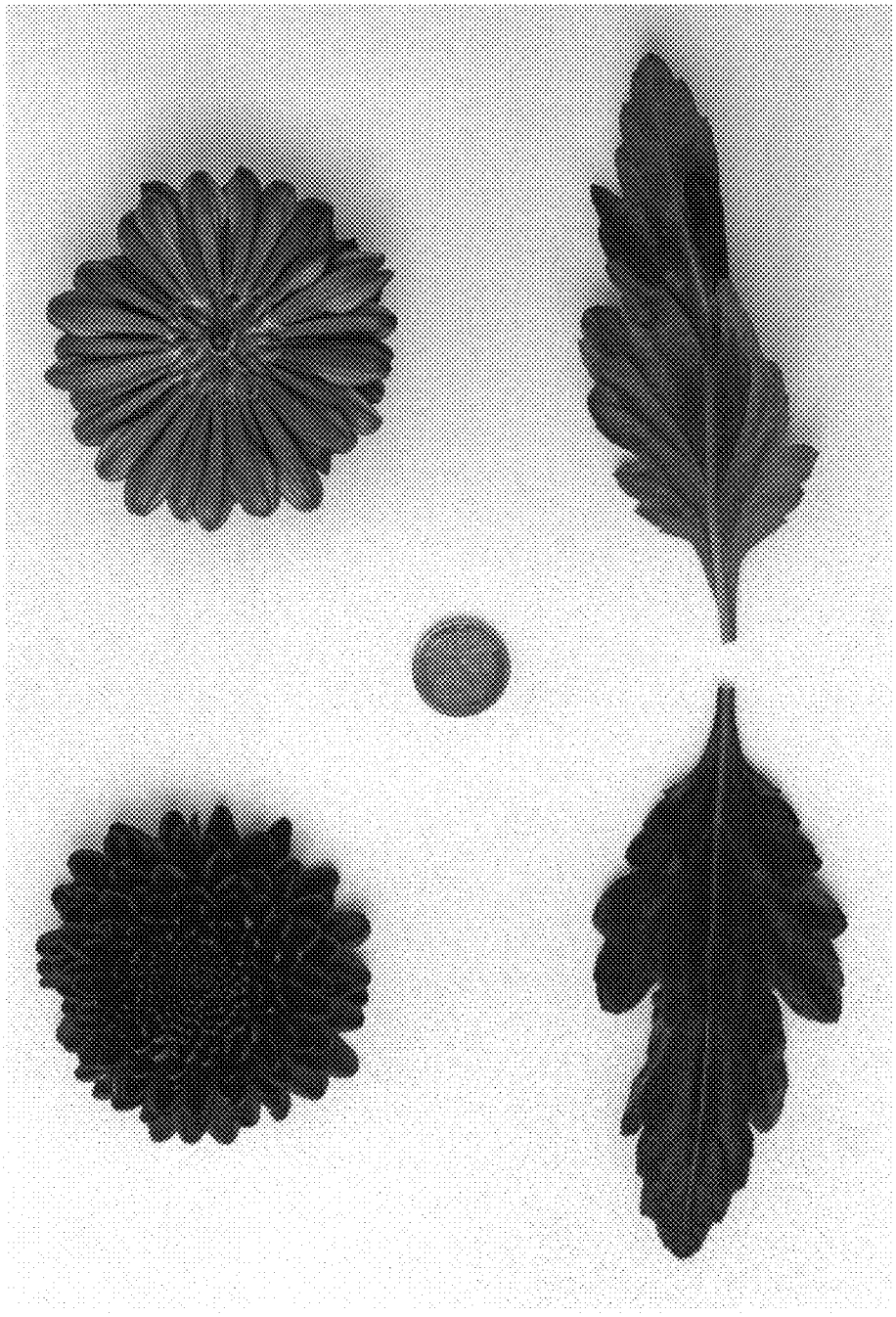

The photograph on the second sheen (FIG. 2 of 2) is a close-up view of lower (top of the photographic sheet) and upper (bottom of the photographic sheet) surfaces of typical inflorescences (left) and leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem disbud-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFGAVI7'.

Parentage:

*Female, or seed, parent*.—Proprietary selection of *Chrysanthemum* x *morifolium* identified as code number DB 33586, not patented.

*Male, or pollen, parent*.—Proprietary selection of *Chrysanthemum* x *morifolium* identified as code number DB 11247, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 76.4 cm.

*Plant height, soil level to top of inflorescence plane*.—About 80.7 cm.

*Plant diameter*.—About 15.2 cm.

*Flowering stem length*.—About 73.2 cm.

*Flowering stem diameter*.—About 6 mm.

*Flowering stem internode length*.—About 2.7 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 144A.

*Flowering stem color, developed*.—Close to 137B; ridges, tinged with close to 197A.

*Leaf description*.—Arrangement: Alternate; simple. Length: About 14.3 cm. Width: About 8.3 cm. Shape: Ovate. Apex: Short apiculate. Base: Attenuate. Margin: Palmately lobed, coarsely crenate; sinuses convergent and shallow in depth. Texture and luster, upper surface: Moderately pubescent, not rugose; moderately velvety; slightly to moderately glossy. Texture and luster, lower surface: Moderately pubescent, prominent venation; slightly velvety; slightly glossy. Venation pattern: Pinnate, reticulate. Color: Developing leaves, upper surface: Close to 137A to 137B. Developing leaves, lower surface: Close to between 138B and 147B. Fully developed leaves, upper surface: Close to between NN137A and 139A;

venation, close to 147B. Fully developed leaves, lower surface: Close to 147B; venation, close to 146C. Petioles: Length: About 2 cm. Diameter: About 3 mm by 3.5 mm. Strength: Moderately strong. Texture and luster, upper and lower surfaces: Densely pubescent; slightly glossy. Color, upper surface: Close to 148B; edges, close to NN137A. Color, lower surface: Close to 147C; edges, close to 137B. Stipules: Quantity and appearance: Two leafy stipules, opposite, at the petiole attachment to the stem. Length: About 9 mm. Width: About 1.3 cm. Shape: Cleft to palmate with two to four lobes. Texture and luster, upper surface: Moderately pubescent, not rugose; moderately velvety; slightly to moderately glossy. Texture and luster, lower surface: Moderately pubescent, prominent venation; slightly velvety; slightly glossy. Color, upper surface: Close to between NN137A and 139A. Color, lower surface: Close to 147B.

Inflorescence description:

*Appearance*.—Decorative incurved inflorescence form with narrowly elliptic to oblanceolate-shaped ray florets; to date, disc floret development has not been observed; inflorescences borne perpendicular to peduncles and face upright; ray florets develop acropetally on a capitulum.

*Fragrance*.—Moderately to faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 57 days later when grown as a disbud-type.

*Postproduction longevity*.—Good postproduction longevity; in an interior environment, inflorescences and foliage will maintain good color and substance for about two weeks; inflorescences persistent.

*Quantity of inflorescences*.—Grown as a disbud-type, all lateral inflorescences are physically removed and only the terminal inflorescence is allowed to develop; if grown as a spray-type, then typically about twelve inflorescences will develop.

*Inflorescence size*.—Diameter: Grown as a disbud type, about 9.1 cm and grown as a spray-type, about 6.8 cm. Depth (height): Grown as a disbud type, about 5.6 cm and grown as a spray-type, about 2.7 cm.

*Receptacles*.—Height: About 6 mm. Diameter: About 1.2 cm. Shape: Flattened globular. Color: Close to 145B and 145D.

*Inflorescence buds*.—Height: About 1.4 cm. Diameter: About 1.3 cm. Shape: Roughly globular. Texture and luster: Distally, smooth and glabrous; proximally, densely pubescent; moderately glossy. Color: Close to 137C; immature ray florets, close to N79B and N79C.

*Ray florets*.—Quantity and arrangement: About 380 arranged in about ten whorls. Length: About 3.5 cm; varying between 1.8 cm and 4.2 cm. Width: About 1 cm; varying between 0.2 cm and 1.2 cm. Shape: Narrowly elliptic to oblanceolate; slightly convex and moderately carinate. Apex: Obtuse to retuse. Base: Attenuate. Margin: Entire; not undulate. Aspect: Initially upright to about 90° from vertical. Texture and luster, upper surface: Smooth, glabrous; velvety; matte. Texture and luster, lower surface: Smooth, glabrous; slightly velvety; moderately glossy. Color: When opening, upper surface: Close to between 59A and 187C. When opening, lower surface: Close to 72B. Fully opened, upper surface: Close to between 59A and 187C; venation, close to between 59A and 187C; color does not change with development. Fully opened, lower surface: Close to 70A; venation, close to 70A; color does not change with development.

*Disc florets*.—To date, disc floret development has not been observed on inflorescences of plants of the new *Chrysanthemum*.

*Involucral bracts*.—Quantity and arrangement: About 28 arranged in three whorls. Length: About 1.2 cm. Width: About 4.5 mm. Shape: Narrowly ovate. Apex: Narrowly obtuse. Base: Cuneate. Margin: Entire. Texture and luster, upper surface: Smooth, glabrous; glossy. Texture and luster, lower surface: Densely pubescent; matte. Color, upper and lower surfaces: Close to 137C; margins, translucent and close to 157D.

*Peduncles*.—Length, terminal peduncle: About 3.8 cm. Diameter, terminal peduncle: About 3.5 mm. Length, third peduncle (when grown as a spray-type): About 3.5 cm. Diameter, third peduncle (when grown as a spray-type): About 3 mm. Strength: Strong. Aspect, terminal peduncle: Mostly upright. Aspect, third peduncle (when grown as a spray-type): About 40° from the flowering stem axis. Texture and luster: Densely pubescent; moderately glossy. Color: Close to 143A.

*Reproductive organs*.—Androecium: Not observed on ray florets. Gynoecium: Quantity: One per ray floret. Pistil length: About 7 mm. Style length: About 6 mm. Style color: Close to 145D. Stigma diameter: About 1 mm. Stigma shape: Cleft, decurrent. Stigma color: Close to 153D. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be relatively resistant to *Fusarium oxysporum* f. sp. *chrysanthemi, Verticillium dahliae* and *Puccinia horiana* strain PhNL1. To date, plants of the new *Chrysanthemum* have not been observed to be resistant to pests and other pathogens common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFGAVI7' as illustrated and described.

* * * * *